(12) United States Patent
Talbert et al.

(10) Patent No.: US 10,670,248 B2
(45) Date of Patent: *Jun. 2, 2020

(54) CONTROLLING THE INTEGRAL LIGHT ENERGY OF A LASER PULSE

(71) Applicant: DePuy Synthes Products, Inc., Raynham, MA (US)

(72) Inventors: Joshua D. Talbert, Salt Lake City, UT (US); Donald M. Wichern, Salt Lake City, UT (US); Laurent Blanquart, Westlake Village, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 345 days.

This patent is subject to a terminal disclaimer.

(21) Appl. No.: 15/722,997

(22) Filed: Oct. 2, 2017

(65) Prior Publication Data
US 2018/0023791 A1 Jan. 25, 2018

Related U.S. Application Data

(63) Continuation of application No. 14/214,795, filed on Mar. 15, 2014, now Pat. No. 9,777,913.
(Continued)

(51) Int. Cl.
*F21V 23/00* (2015.01)
*A61B 1/06* (2006.01)
*A61B 1/07* (2006.01)

(52) U.S. Cl.
CPC .......... *F21V 23/003* (2013.01); *A61B 1/063* (2013.01); *A61B 1/0661* (2013.01); *A61B 1/0684* (2013.01); *A61B 1/07* (2013.01)

(58) Field of Classification Search
CPC ... A61B 1/0638; A61B 1/0661; A61B 1/0684; A61B 1/07; A61B 1/00009;
(Continued)

(56) References Cited

U.S. PATENT DOCUMENTS 3,666,885 A 5/1972 Hemsley et al.
4,011,403 A 3/1977 Epstein et al.
(Continued)

FOREIGN PATENT DOCUMENTS

CN 1520696 A 8/2004
CN 101079966 A 11/2007
(Continued)

OTHER PUBLICATIONS

Blumenfeld, et al. Three-dimensional image registration of MR proximal femur images for the analysis of trabecular bone parameters. Oct. 2008. [retrieved on Jul. 30, 2014] Retrieved from the internet: <URL: http://www.ncbi.nlm.nih.gov/pmc/articles/PMC2673590/>.

*Primary Examiner* — John P Leubecker
(74) *Attorney, Agent, or Firm* — Terrence J. Edwards; TechLaw Ventures, PLLC

(57) ABSTRACT

An embodiment of a system for providing illumination for an endoscope device includes a light source comprising laser bundles each having laser light emitters, an electromagnetic sensor embedded within the light source to sense electromagnetic energy emitted from at least one laser light emitter within each of the laser bundles, and a control circuit in electronic communication with the electromagnetic sensor and at least one laser light emitter. The light source sequentially pulses electromagnetic energy in a plurality of individual electromagnetic partitions. The electromagnetic sensor receives electromagnetic energy from at least one laser light emitter and measures an amount of electromagnetic energy generated by at least one laser light emitter.

26 Claims, 7 Drawing Sheets

Related U.S. Application Data

(60) Provisional application No. 61/799,626, filed on Mar. 15, 2013.

(58) Field of Classification Search
CPC . A61B 1/00043; A61B 1/00045; A61B 1/045; F21V 23/003; F21V 23/0457; H04N 5/2628; H04N 5/23296
See application file for complete search history.

(56) References Cited

U.S. PATENT DOCUMENTS

| | | | |
|---|---|---|---|
| 4,363,963 A | 12/1982 | Ando | |
| 4,433,675 A | 2/1984 | Konoshima | |
| 4,436,095 A | 3/1984 | Kruger | |
| 4,473,839 A | 9/1984 | Noda | |
| 4,644,403 A | 2/1987 | Sakai et al. | |
| 4,651,226 A | 3/1987 | Motoori et al. | |
| 4,692,606 A | 9/1987 | Sakai et al. | |
| 4,740,837 A | 4/1988 | Yanagisawa et al. | |
| 4,741,327 A | 5/1988 | Yabe | |
| 4,742,388 A | 5/1988 | Cooper et al. | |
| 4,745,471 A | 5/1988 | Takamura et al. | |
| 4,773,396 A | 9/1988 | Okazaki | |
| 4,782,386 A | 11/1988 | Ams et al. | |
| 4,786,965 A | 11/1988 | Yabe | |
| 4,832,003 A | 5/1989 | Yabe | |
| 4,845,555 A | 7/1989 | Yabe et al. | |
| 4,853,772 A | 8/1989 | Kikuchi | |
| 4,853,773 A | 8/1989 | Hibino et al. | |
| 4,866,526 A | 9/1989 | Ams et al. | |
| 4,884,133 A | 11/1989 | Kanno et al. | |
| 4,884,134 A | 11/1989 | Tsuji et al. | |
| 4,918,521 A | 4/1990 | Yabe et al. | |
| 4,924,856 A | 5/1990 | Noguchi | |
| 4,938,205 A | 7/1990 | Nudelman | |
| 4,942,473 A | 7/1990 | Zeevi et al. | |
| 4,947,246 A | 8/1990 | Kikuchi | |
| 4,953,539 A | 9/1990 | Nakamura et al. | |
| 4,959,710 A | 9/1990 | Uehara et al. | |
| 5,001,556 A | 3/1991 | Nakamura et al. | |
| 5,016,975 A | 5/1991 | Sasaki et al. | |
| 5,021,888 A | 6/1991 | Kondou et al. | |
| 5,047,846 A | 9/1991 | Uchiyama et al. | |
| RE33,854 E | 3/1992 | Adair | |
| 5,103,497 A | 4/1992 | Hicks | |
| 5,111,804 A | 5/1992 | Funakoshi | |
| 5,133,035 A | 7/1992 | Hicks | |
| 5,187,572 A | 2/1993 | Nakamura et al. | |
| 5,188,094 A | 2/1993 | Adair | |
| 5,196,938 A | 3/1993 | Blessinger | |
| 5,200,838 A | 4/1993 | Nudelman et al. | |
| 5,220,198 A | 6/1993 | Tsuji | |
| 5,228,430 A | 7/1993 | Sakamoto | |
| 5,233,416 A | 8/1993 | Inoue | |
| 5,241,170 A | 8/1993 | Field, Jr. et al. | |
| 5,264,925 A | 11/1993 | Shipp et al. | |
| 5,313,306 A | 5/1994 | Kuban et al. | |
| 5,325,847 A | 7/1994 | Matsuno | |
| 5,365,268 A | 11/1994 | Minami | |
| 5,402,768 A | 4/1995 | Adair | |
| 5,408,268 A | 4/1995 | Shipp | |
| 5,411,020 A | 5/1995 | Ito | |
| 5,427,087 A | 6/1995 | Ito et al. | |
| 5,454,366 A | 10/1995 | Ito et al. | |
| 5,494,483 A | 2/1996 | Adair | |
| 5,523,786 A | 6/1996 | Parulski | |
| 5,550,595 A | 8/1996 | Hannah | |
| 5,594,497 A | 1/1997 | Ahern et al. | |
| 5,665,959 A | 9/1997 | Fossum et al. | |
| 5,704,836 A | 1/1998 | Norton et al. | |
| 5,730,702 A | 3/1998 | Tanaka et al. | |
| 5,734,418 A | 3/1998 | Danna | |
| 5,748,234 A | 5/1998 | Lippincott | |
| 5,749,830 A | 5/1998 | Kaneko et al. | |
| 5,754,313 A | 5/1998 | Pelchy et al. | |
| 5,783,909 A | 7/1998 | Hochstein | |
| 5,784,099 A | 7/1998 | Lippincott | |
| 5,857,963 A | 1/1999 | Pelchy et al. | |
| 5,887,049 A | 3/1999 | Fossum | |
| 5,929,901 A | 7/1999 | Adair et al. | |
| 5,949,483 A | 9/1999 | Fossum et al. | |
| 5,986,693 A | 11/1999 | Adair et al. | |
| 6,023,315 A | 2/2000 | Harrold et al. | |
| 6,038,067 A | 3/2000 | George | |
| 6,043,839 A | 3/2000 | Adair et al. | |
| 6,139,489 A | 10/2000 | Wampler et al. | |
| 6,142,930 A | 11/2000 | Ito et al. | |
| 6,166,768 A | 12/2000 | Fossum et al. | |
| 6,184,922 B1 | 2/2001 | Saito et al. | |
| 6,184,940 B1 | 2/2001 | Sano | |
| 6,215,517 B1 | 3/2001 | Takahashi et al. | |
| 6,222,175 B1 | 4/2001 | Krymski | |
| 6,239,456 B1 | 5/2001 | Berezin et al. | |
| 6,272,269 B1 | 8/2001 | Naum | |
| 6,275,255 B1 | 8/2001 | Adair et al. | |
| 6,292,220 B1 | 9/2001 | Ogawa et al. | |
| 6,294,775 B1 | 9/2001 | Seibel et al. | |
| 6,310,642 B1 | 10/2001 | Adair et al. | |
| 6,320,331 B1 | 11/2001 | Iida et al. | |
| 6,331,156 B1 | 12/2001 | Haefele et al. | |
| 6,389,205 B1 | 5/2002 | Muckner et al. | |
| 6,416,463 B1 | 7/2002 | Tsuzuki et al. | |
| 6,429,953 B1 | 8/2002 | Feng | |
| 6,444,970 B1 | 9/2002 | Barbato | |
| 6,445,022 B1 | 9/2002 | Barna et al. | |
| 6,445,139 B1 | 9/2002 | Marshall et al. | |
| 6,464,633 B1 | 10/2002 | Hosoda et al. | |
| 6,466,618 B1 | 10/2002 | Messing et al. | |
| 6,485,414 B1 | 11/2002 | Neuberger | |
| 6,512,280 B2 | 1/2003 | Chen et al. | |
| 6,567,115 B1 | 5/2003 | Miyashita et al. | |
| 6,627,474 B2 | 9/2003 | Barna et al. | |
| 6,631,230 B1 | 10/2003 | Campbell | |
| 6,659,940 B2 | 12/2003 | Adler | |
| 6,665,013 B1 | 12/2003 | Fossum et al. | |
| 6,677,992 B1 | 1/2004 | Matsumoto et al. | |
| 6,690,466 B2 | 2/2004 | Miller et al. | |
| 6,692,431 B2 | 2/2004 | Kazakevich | |
| 6,707,499 B1 | 3/2004 | Kung et al. | |
| 6,772,181 B1 | 8/2004 | Fu et al. | |
| 6,773,392 B2 | 8/2004 | Kikuchi et al. | |
| 6,791,739 B2 | 9/2004 | Ramanujan et al. | |
| 6,796,939 B1 | 9/2004 | Hirata et al. | |
| 6,799,065 B1 | 9/2004 | Niemeyer | |
| 6,809,358 B2 | 10/2004 | Hsieh et al. | |
| 6,838,653 B2 | 1/2005 | Campbell et al. | |
| 6,841,947 B2 | 1/2005 | Berg-johansen | |
| 6,847,399 B1 | 1/2005 | Ang | |
| 6,856,712 B2 | 2/2005 | Fauver et al. | |
| 6,873,363 B1 | 3/2005 | Barna et al. | |
| 6,879,340 B1 | 4/2005 | Chevallier | |
| 6,899,675 B2 | 5/2005 | Cline et al. | |
| 6,900,829 B1 | 5/2005 | Orzawa et al. | |
| 6,906,745 B1 | 6/2005 | Fossum et al. | |
| 6,921,920 B2 | 7/2005 | Kazakevich | |
| 6,933,974 B2 | 8/2005 | Lee | |
| 6,947,090 B2 | 9/2005 | Komoro et al. | |
| 6,961,461 B2 | 11/2005 | MacKinnon et al. | |
| 6,970,195 B1 | 11/2005 | Bidermann et al. | |
| 6,977,733 B2 | 12/2005 | Denk et al. | |
| 6,982,740 B2 | 1/2006 | Adair et al. | |
| 6,998,594 B2 * | 2/2006 | Gaines | H05B 33/0869 250/205 |
| 6,999,118 B2 | 2/2006 | Suzuki | |
| 7,009,634 B2 | 3/2006 | Iddan et al. | |
| 7,009,648 B2 | 3/2006 | Lauxtermann et al. | |
| 7,030,904 B2 | 4/2006 | Adair et al. | |
| 7,037,259 B2 | 5/2006 | Hakamata et al. | |
| 7,068,878 B2 | 6/2006 | Crossman-Bosworth et al. | |
| 7,071,979 B1 | 7/2006 | Ohtani et al. | |
| 7,079,178 B2 | 7/2006 | Hynecek | |
| 7,102,682 B2 | 9/2006 | Baer | |
| 7,105,371 B2 | 9/2006 | Fossum et al. | |

(56) References Cited

U.S. PATENT DOCUMENTS

| | | |
|---|---|---|
| 7,106,377 B2 | 9/2006 | Bean et al. |
| 7,119,839 B1 | 10/2006 | Mansoorian |
| 7,151,568 B2 | 12/2006 | Kawachi et al. |
| 7,159,782 B2 | 1/2007 | Johnston et al. |
| 7,184,084 B2 | 2/2007 | Glenn |
| 7,189,226 B2 | 3/2007 | Auld et al. |
| 7,189,961 B2 | 3/2007 | Johnston et al. |
| 7,208,983 B2 | 4/2007 | Imaizumi et al. |
| 7,252,236 B2 | 8/2007 | Johnston et al. |
| 7,258,663 B2 | 8/2007 | Doguchi et al. |
| 7,261,687 B2 | 8/2007 | Yang |
| 7,280,139 B2 | 10/2007 | Pahr et al. |
| 7,298,938 B2 | 11/2007 | Johnston |
| 7,312,879 B2 | 12/2007 | Johnston |
| 7,319,478 B2 | 1/2008 | Dolt et al. |
| 7,355,155 B2 | 4/2008 | Wang |
| 7,356,198 B2 | 4/2008 | Chauville et al. |
| 7,365,768 B1 | 4/2008 | Ono et al. |
| 7,369,140 B1 | 5/2008 | King et al. |
| 7,369,176 B2 | 5/2008 | Sonnenschein et al. |
| 7,455,638 B2 | 11/2008 | Ogawa et al. |
| 7,470,229 B2 | 12/2008 | Ogawa et al. |
| 7,476,197 B2 | 1/2009 | Wiklof et al. |
| 7,532,760 B2 | 5/2009 | Kaplinsky et al. |
| 7,540,645 B2 | 5/2009 | Choi |
| 7,544,163 B2 | 6/2009 | MacKinnon et al. |
| 7,545,434 B2 | 6/2009 | Bean et al. |
| 7,564,935 B2 | 7/2009 | Suzuki |
| 7,567,291 B2 | 7/2009 | Bechtel et al. |
| 7,573,516 B2 | 8/2009 | Krymski et al. |
| 7,573,519 B2 | 8/2009 | Phan et al. |
| 7,583,872 B2 | 9/2009 | Seibel et al. |
| 7,630,008 B2 | 12/2009 | Sarwari |
| 7,744,528 B2 | 6/2010 | Wallace et al. |
| 7,783,133 B2 | 8/2010 | Dunki-Jacobs et al. |
| 7,784,697 B2 | 8/2010 | Johnston et al. |
| 7,791,009 B2 | 9/2010 | Johnston et al. |
| 7,792,378 B2 | 9/2010 | Liege et al. |
| 7,794,394 B2 | 9/2010 | Frangioni |
| 7,813,538 B2 | 10/2010 | Carroll et al. |
| 7,914,447 B2 | 3/2011 | Kanai |
| 7,916,193 B2 | 3/2011 | Fossum |
| 7,935,050 B2 | 5/2011 | Luanava et al. |
| 7,944,566 B2 | 5/2011 | Xie |
| 7,969,097 B2 | 6/2011 | Van De Ven |
| 7,995,123 B2 | 8/2011 | Lee et al. |
| 8,040,394 B2 | 10/2011 | Fossum et al. |
| 8,054,339 B2 | 11/2011 | Fossum et al. |
| 8,059,174 B2 | 11/2011 | Mann et al. |
| 8,100,826 B2 | 1/2012 | MacKinnon et al. |
| 8,159,584 B2 | 4/2012 | Iwabuchi et al. |
| 8,193,542 B2 | 6/2012 | Machara |
| 8,212,884 B2 | 7/2012 | Seibel et al. |
| 8,231,522 B2 | 7/2012 | Endo et al. |
| 8,300,111 B2 | 10/2012 | Iwane |
| 8,372,003 B2 | 2/2013 | St. George et al. |
| 8,382,662 B2 | 2/2013 | Soper et al. |
| 8,396,535 B2 | 3/2013 | Wang et al. |
| 8,423,110 B2 | 4/2013 | Barbato et al. |
| 8,471,938 B2 | 6/2013 | Altice, Jr. et al. |
| 8,476,575 B2 | 7/2013 | Mokhnatyuk |
| 8,482,823 B2 | 7/2013 | Cheng |
| 8,493,474 B2 | 7/2013 | Richardson |
| 8,493,564 B2 | 7/2013 | Brukilacchio et al. |
| 8,523,367 B2 | 9/2013 | Ogura |
| 8,537,203 B2 | 9/2013 | Seibel et al. |
| 8,559,743 B2 | 10/2013 | Liege et al. |
| 8,582,011 B2 | 11/2013 | Dosluoglu |
| 8,602,971 B2 | 12/2013 | Farr |
| 8,605,177 B2 | 12/2013 | Rossi et al. |
| 8,610,808 B2 | 12/2013 | Prescher et al. |
| 8,614,754 B2 | 12/2013 | Fossum |
| 8,625,016 B2 | 1/2014 | Fossum et al. |
| 8,638,847 B2 | 1/2014 | Wang |
| 8,648,287 B1 | 2/2014 | Fossum |
| 8,649,848 B2 | 2/2014 | Crane et al. |
| 8,668,339 B2 | 3/2014 | Kabuki et al. |
| 8,675,125 B2 | 3/2014 | Cossairt et al. |
| 8,698,887 B2 | 4/2014 | Makino et al. |
| 8,836,834 B2 | 9/2014 | Hashimoto et al. |
| 8,848,063 B2 | 9/2014 | Jo et al. |
| 8,858,425 B2 | 10/2014 | Farr et al. |
| 8,885,034 B2 | 11/2014 | Adair et al. |
| 9,509,917 B2 | 11/2016 | Blanquart et al. |
| 9,516,239 B2 | 12/2016 | Blanquart et al. |
| 9,762,879 B2 | 9/2017 | Blanquart et al. |
| 9,777,913 B2 | 10/2017 | Talbert et al. |
| 2001/0017649 A1 | 8/2001 | Yaron |
| 2001/0030744 A1 | 10/2001 | Chang |
| 2001/0055462 A1 | 12/2001 | Seibel |
| 2002/0054219 A1 | 5/2002 | Jaspers |
| 2002/0064341 A1 | 5/2002 | Fauver et al. |
| 2002/0080248 A1 | 6/2002 | Adair et al. |
| 2002/0080359 A1 | 6/2002 | Denk et al. |
| 2002/0140844 A1 | 10/2002 | Kurokawa et al. |
| 2002/0158976 A1 | 10/2002 | Vni et al. |
| 2002/0158986 A1 | 10/2002 | Baer |
| 2003/0007087 A1 | 1/2003 | Hakamata et al. |
| 2003/0007686 A1 | 1/2003 | Roever |
| 2003/0107664 A1 | 6/2003 | Suzuki |
| 2003/0189663 A1 | 10/2003 | Dolt et al. |
| 2004/0082833 A1 | 4/2004 | Adler et al. |
| 2004/0170712 A1 | 9/2004 | Sadek El Mogy |
| 2005/0009982 A1 | 1/2005 | Inagaki et al. |
| 2005/0027164 A1 | 2/2005 | Barbato et al. |
| 2005/0038322 A1 | 2/2005 | Banik |
| 2005/0113641 A1 | 5/2005 | Bala |
| 2005/0122530 A1 | 6/2005 | Denk et al. |
| 2005/0151866 A1 | 7/2005 | Ando et al. |
| 2005/0200291 A1 | 9/2005 | Naugler, Jr. et al. |
| 2005/0234302 A1 | 10/2005 | MacKinnon et al. |
| 2005/0237384 A1 | 10/2005 | Jess et al. |
| 2005/0261552 A1 | 11/2005 | Mori et al. |
| 2005/0288546 A1 | 12/2005 | Sonnenschein et al. |
| 2006/0069314 A1 | 3/2006 | Farr |
| 2006/0087841 A1 | 4/2006 | Chern et al. |
| 2006/0197664 A1 | 9/2006 | Zhang et al. |
| 2006/0202036 A1 | 9/2006 | Wang et al. |
| 2006/0221250 A1 | 10/2006 | Rossbach et al. |
| 2006/0226231 A1 | 10/2006 | Johnston et al. |
| 2006/0264734 A1 | 11/2006 | Kimoto et al. |
| 2006/0274335 A1 | 12/2006 | Wittenstein |
| 2007/0010712 A1 | 1/2007 | Negishi |
| 2007/0041448 A1 | 2/2007 | Miller et al. |
| 2007/0083085 A1 | 4/2007 | Birnkrant et al. |
| 2007/0129601 A1 | 6/2007 | Johnston et al. |
| 2007/0147033 A1 | 6/2007 | Ogawa et al. |
| 2007/0244364 A1 | 10/2007 | Luanava et al. |
| 2007/0244365 A1 | 10/2007 | Wiklof |
| 2007/0276187 A1 | 11/2007 | Wiklof et al. |
| 2007/0279486 A1 | 12/2007 | Bayer et al. |
| 2007/0285526 A1 | 12/2007 | Mann et al. |
| 2007/0293720 A1 | 12/2007 | Bayer |
| 2008/0045800 A2 | 2/2008 | Farr |
| 2008/0088719 A1 | 4/2008 | Jacob et al. |
| 2008/0107333 A1 | 5/2008 | Mazinani et al. |
| 2008/0136953 A1 | 6/2008 | Barnea et al. |
| 2008/0158348 A1 | 7/2008 | Karpen et al. |
| 2008/0165360 A1 | 7/2008 | Johnston |
| 2008/0192131 A1 | 8/2008 | Kim et al. |
| 2008/0218598 A1 | 9/2008 | Harada et al. |
| 2008/0218615 A1 | 9/2008 | Huang et al. |
| 2008/0218824 A1 | 9/2008 | Johnston et al. |
| 2008/0249369 A1 | 10/2008 | Seibel et al. |
| 2009/0012361 A1 | 1/2009 | MacKinnon et al. |
| 2009/0012368 A1 | 1/2009 | Banik |
| 2009/0021588 A1 | 1/2009 | Border et al. |
| 2009/0024000 A1 | 1/2009 | Chen |
| 2009/0028465 A1 | 1/2009 | Pan |
| 2009/0074265 A1 | 3/2009 | Huang et al. |
| 2009/0091645 A1 | 4/2009 | Trimeche et al. |
| 2009/0137893 A1 | 5/2009 | Seibel et al. |
| 2009/0147077 A1 | 6/2009 | Tani et al. |
| 2009/0154886 A1 | 6/2009 | Lewis et al. |

(56) References Cited

U.S. PATENT DOCUMENTS

| | | |
|---|---|---|
| 2009/0160976 A1 | 6/2009 | Chen et al. |
| 2009/0189530 A1 | 7/2009 | Ashdown et al. |
| 2009/0208143 A1 | 8/2009 | Yoon et al. |
| 2009/0227847 A1 | 9/2009 | Tepper et al. |
| 2009/0232213 A1 | 9/2009 | Jia |
| 2009/0259102 A1 | 10/2009 | Koninckx et al. |
| 2009/0268063 A1 | 10/2009 | Ellis-Monaghan et al. |
| 2009/0292168 A1 | 11/2009 | Farr |
| 2009/0309500 A1 | 12/2009 | Reisch |
| 2009/0316116 A1 | 12/2009 | Melville et al. |
| 2009/0322912 A1 | 12/2009 | Blanquart |
| 2010/0026722 A1 | 2/2010 | Kondo |
| 2010/0049180 A1 | 2/2010 | Wells et al. |
| 2010/0069713 A1 | 3/2010 | Endo et al. |
| 2010/0102199 A1 | 4/2010 | Negley et al. |
| 2010/0121142 A1 | 5/2010 | OuYang et al. |
| 2010/0121143 A1 | 5/2010 | Sugimoto et al. |
| 2010/0123775 A1 | 5/2010 | Shibasaki |
| 2010/0134608 A1 | 6/2010 | Shibasaki |
| 2010/0134662 A1 | 6/2010 | Bub |
| 2010/0135398 A1 | 6/2010 | Wittmann et al. |
| 2010/0137684 A1 | 6/2010 | Shibasaki et al. |
| 2010/0149421 A1 | 6/2010 | Lin et al. |
| 2010/0157037 A1 | 6/2010 | Iketani et al. |
| 2010/0157039 A1 | 6/2010 | Sugai |
| 2010/0165087 A1 | 7/2010 | Corso et al. |
| 2010/0171429 A1 | 7/2010 | Garcia et al. |
| 2010/0182446 A1 | 7/2010 | Matsubayashi |
| 2010/0198009 A1 | 8/2010 | Farr et al. |
| 2010/0198134 A1 | 8/2010 | Eckhouse et al. |
| 2010/0201797 A1 | 8/2010 | Shizukuishi et al. |
| 2010/0228089 A1 | 9/2010 | Hoffman et al. |
| 2010/0261961 A1 | 10/2010 | Scott et al. |
| 2010/0274082 A1 | 10/2010 | Iguchi et al. |
| 2010/0274090 A1 | 10/2010 | Ozaki et al. |
| 2010/0305406 A1 | 12/2010 | Braun et al. |
| 2010/0309333 A1 | 12/2010 | Smith et al. |
| 2011/0028790 A1 | 2/2011 | Farr et al. |
| 2011/0063483 A1 | 3/2011 | Rossi et al. |
| 2011/0122301 A1 | 5/2011 | Yamura et al. |
| 2011/0149358 A1 | 6/2011 | Cheng |
| 2011/0181709 A1 | 7/2011 | Wright et al. |
| 2011/0181840 A1 | 7/2011 | Cobb |
| 2011/0184239 A1 | 7/2011 | Wright et al. |
| 2011/0184243 A1 | 7/2011 | Wright et al. |
| 2011/0208004 A1 | 8/2011 | Feingold et al. |
| 2011/0212649 A1 | 9/2011 | Stokoe et al. |
| 2011/0237882 A1 | 9/2011 | Saito |
| 2011/0237884 A1 | 9/2011 | Saito |
| 2011/0245605 A1 | 10/2011 | Jacobsen et al. |
| 2011/0245616 A1 | 10/2011 | Kobayashi |
| 2011/0255844 A1 | 10/2011 | Wu et al. |
| 2011/0274175 A1 | 11/2011 | Sumitomo |
| 2011/0279679 A1 | 11/2011 | Samuel et al. |
| 2011/0288374 A1 | 11/2011 | Hadani et al. |
| 2011/0291564 A1* | 12/2011 | Huang ............... F21V 23/0457 315/77 |
| 2011/0292258 A1 | 12/2011 | Adler et al. |
| 2011/0295061 A1 | 12/2011 | Haramaty et al. |
| 2012/0004508 A1 | 1/2012 | McDowall et al. |
| 2012/0014563 A1 | 1/2012 | Bendall |
| 2012/0029279 A1 | 2/2012 | Kucklick |
| 2012/0033118 A1 | 2/2012 | Lee et al. |
| 2012/0041267 A1 | 2/2012 | Benning et al. |
| 2012/0041534 A1 | 2/2012 | Clerc et al. |
| 2012/0050592 A1 | 3/2012 | Oguma |
| 2012/0078052 A1 | 3/2012 | Cheng |
| 2012/0098933 A1 | 4/2012 | Robinson et al. |
| 2012/0104230 A1 | 5/2012 | Eismann et al. |
| 2012/0113506 A1 | 5/2012 | Gmitro et al. |
| 2012/0120282 A1 | 5/2012 | Goris |
| 2012/0140302 A1 | 6/2012 | Xie et al. |
| 2012/0155761 A1 | 6/2012 | Matsuoka |
| 2012/0157774 A1 | 6/2012 | Kaku |
| 2012/0194686 A1 | 8/2012 | Liu et al. |
| 2012/0197080 A1 | 8/2012 | Murayama |
| 2012/0242975 A1 | 9/2012 | Min et al. |
| 2012/0262621 A1 | 10/2012 | Sato et al. |
| 2012/0281111 A1 | 11/2012 | Jo et al. |
| 2013/0018256 A1 | 1/2013 | Kislev et al. |
| 2013/0035545 A1 | 2/2013 | Ono |
| 2013/0053642 A1 | 2/2013 | Mizuyoshi et al. |
| 2013/0070071 A1 | 3/2013 | Peltie et al. |
| 2013/0126708 A1 | 5/2013 | Blanquart |
| 2013/0127934 A1 | 5/2013 | Chiang |
| 2013/0135589 A1 | 5/2013 | Curtis et al. |
| 2013/0144120 A1 | 6/2013 | Yamazaki |
| 2013/0155215 A1 | 6/2013 | Shimada et al. |
| 2013/0155305 A1 | 6/2013 | Shintani |
| 2013/0158346 A1 | 6/2013 | Soper et al. |
| 2013/0184524 A1 | 7/2013 | Shimada et al. |
| 2013/0211217 A1 | 8/2013 | Yamaguchi et al. |
| 2013/0242069 A1 | 9/2013 | Kobayashi |
| 2013/0244453 A1 | 9/2013 | Sakamoto |
| 2013/0274597 A1 | 10/2013 | Byrne et al. |
| 2013/0296652 A1 | 11/2013 | Farr |
| 2013/0300837 A1 | 11/2013 | DiCarlo et al. |
| 2013/0342690 A1 | 12/2013 | Williams et al. |
| 2014/0022365 A1 | 1/2014 | Yoshino |
| 2014/0031623 A1 | 1/2014 | Kagaya |
| 2014/0005532 A1 | 2/2014 | Choi et al. |
| 2014/0052004 A1 | 2/2014 | D'Alfonso et al. |
| 2014/0073852 A1 | 3/2014 | Banik et al. |
| 2014/0073853 A1 | 3/2014 | Swisher et al. |
| 2014/0078278 A1 | 3/2014 | Lei |
| 2014/0088363 A1 | 3/2014 | Sakai et al. |
| 2014/0104466 A1 | 4/2014 | Fossum |
| 2014/0110485 A1 | 4/2014 | Toa et al. |
| 2014/0160318 A1 | 6/2014 | Blanquart et al. |
| 2014/0163319 A1 | 6/2014 | Blanquart et al. |
| 2014/0203084 A1 | 7/2014 | Wang |
| 2014/0225215 A1 | 8/2014 | Chien et al. |
| 2014/0267655 A1 | 9/2014 | Richardson et al. |
| 2014/0267851 A1 | 9/2014 | Rhoads |
| 2014/0268860 A1 | 9/2014 | Talbert et al. |
| 2014/0288365 A1 | 9/2014 | Henley et al. |
| 2014/0300698 A1 | 10/2014 | Wany |
| 2014/0316199 A1 | 10/2014 | Kucklick |
| 2014/0354788 A1 | 12/2014 | Yano |
| 2014/0364689 A1 | 12/2014 | Adair et al. |
| 2015/0237245 A1 | 8/2015 | Renard et al. |
| 2015/0271370 A1 | 9/2015 | Henley et al. |
| 2016/0183775 A1 | 6/2016 | Blanquart et al. |
| 2017/0085853 A1 | 3/2017 | Blanquart et al. |
| 2017/0230574 A1 | 8/2017 | Richardson et al. |

FOREIGN PATENT DOCUMENTS

| | | |
|---|---|---|
| CN | 101449575 A | 6/2009 |
| CN | 101755448 A | 6/2010 |
| CN | 102469932 A | 5/2012 |
| EP | 0660616 A2 | 6/1995 |
| EP | 0904725 A1 | 3/1999 |
| EP | 1079255 A2 | 2/2001 |
| EP | 1637062 A1 | 3/2006 |
| EP | 1712177 A1 | 10/2006 |
| EP | 1819151 A1 | 8/2007 |
| EP | 2359739 A1 | 8/2011 |
| EP | 2371268 A1 | 8/2011 |
| JP | 63-234941 | 9/1988 |
| JP | 2001-308531 A | 11/2001 |
| JP | 2002-020816 A | 1/2002 |
| JP | 2007-029746 A | 2/2007 |
| JP | 2007-240931 A | 9/2007 |
| JP | 2009-537283 A | 10/2009 |
| JP | 2010-068992 A | 4/2010 |
| JP | 2010-125284 A | 6/2010 |
| JP | 2011-055327 A | 3/2011 |
| JP | 2012-000160 A | 1/2012 |
| JP | 2011-267098 A | 6/2013 |
| MX | 2015001195 A | 1/2016 |
| WO | 1996005693 | 2/1996 |

(56) References Cited

FOREIGN PATENT DOCUMENTS

| | | |
|---|---|---|
| WO | 2009120228 A1 | 10/2009 |
| WO | 2012043771 A1 | 4/2012 |

\* cited by examiner

CONTROLLING THE INTEGRAL LIGHT ENERGY OF A LASER PULSE

CROSS-REFERENCE TO RELATED APPLICATIONS

This application is a continuation of U.S. patent application Ser. No. 14/214,795, filed Mar. 15, 2014 (now U.S. Pat. No. 9,777,913, issued Oct. 3, 2017) and claims the benefit of U.S. Provisional Application No. 61/799,626, filed Mar. 15, 2013, which are incorporated herein by reference in their entirety, including but not limited to those portions that specifically appear hereinafter, the incorporation by reference being made with the following exception: In the event that any portion of any of the above-referenced applications is inconsistent with this application, this application supersedes said above-referenced applications.

STATEMENT REGARDING FEDERALLY SPONSORED RESEARCH OR DEVELOPMENT

Not Applicable.

BACKGROUND

Advances in technology have provided advances in imaging capabilities for medical use. One area that has enjoyed some of the most beneficial advances is that of endoscopic surgical procedures because of the advances in the components that make up an endoscope.

The disclosure relates generally to electromagnetic sensing and sensors, and is more particularly related to controlling a consistent amount of electromagnetic energy that may be delivered by an emitter configured to illuminate a scene. The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where.

DETAILED DESCRIPTION

Figure 1:
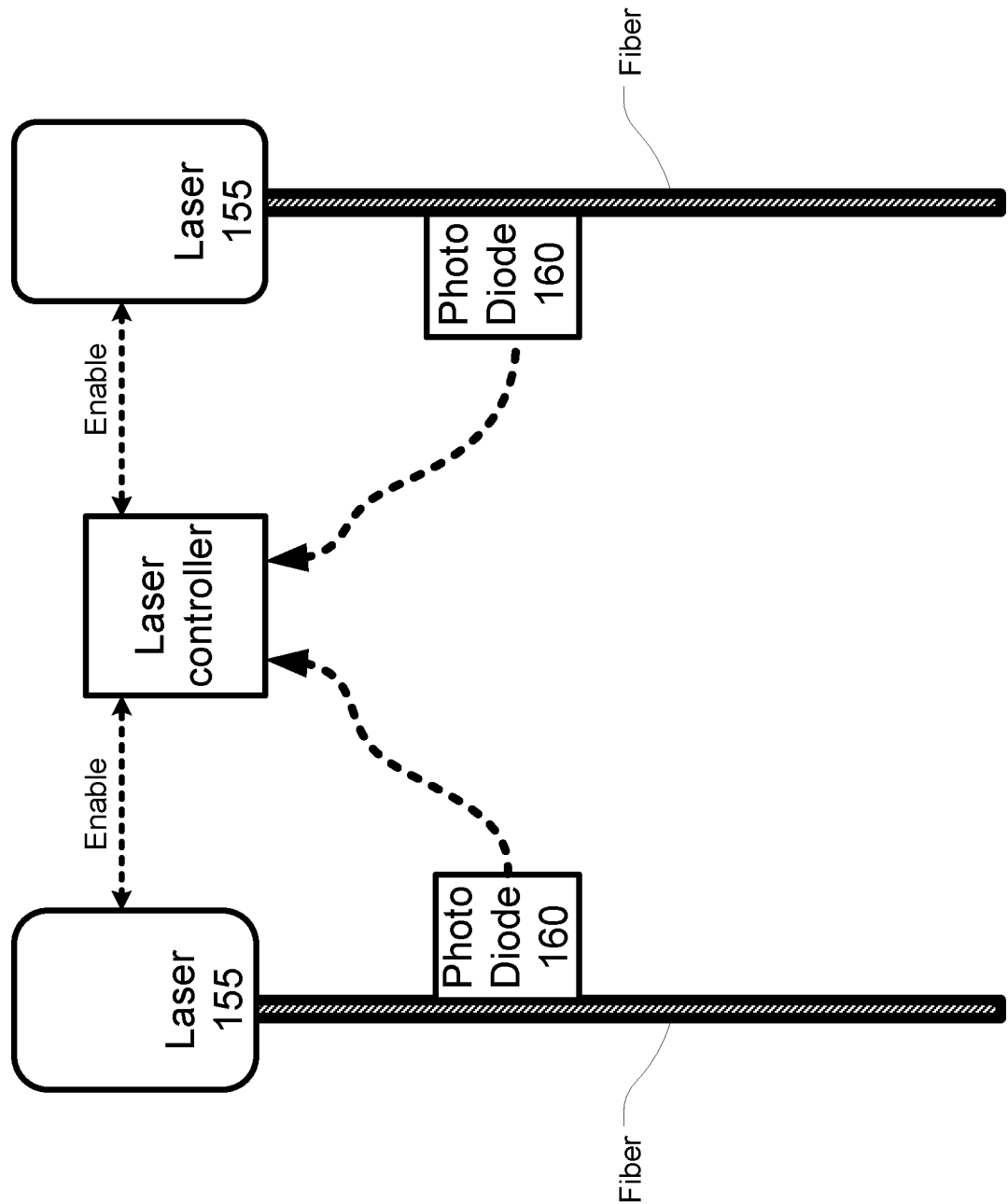
FIG. 1 illustrates an embodiment of a light controller of an illumination system in accordance with the principles and teachings of the disclosure.

The disclosure extends to methods, systems, and computer based products for digital imaging that may be primarily suited to medical, industrial, marine, and automotive applications. In the following description of the disclosure, reference may be made to the accompanying drawings, which form a part hereof, and in which is shown by way of illustration specific implementations in which the disclosure may be practiced. It may be understood that other implementations may be utilized and structural changes may be made without departing from the scope of the disclosure.

The disclosure describes at least one embodiment that can be used to control the duration of a single or multiple light emitting system, such as a laser or other light system, to limit output light energy of a light pulse that is held to a specified tolerance in a light controlled environment where the light pulse is the sole light source available. It will be appreciated that for the sake of simplicity, the disclosure will use a laser as an exemplary embodiment of the light emitter. However, it will be appreciated that the light emitter may be any light source, including a laser, LED or other light source without departing from the scope of the disclosure.

An embodiment may comprise a system for digital imaging within a light deficient environment comprising: a camera control unit that may comprise a microcontroller, FPGA, ASIC, hardware, software, ISP, and the like support circuitry for digital imaging.

The system may further comprise a controllable light source connected to the CCU, wherein the CCU may control enable/disabling, power level, light level, on/off, and other controls of the output of the controllable light source. The light source may comprise digital light sources such as lasers and light emitting diodes, and may also comprise analog light sources.

The system may further comprise an imaging sensor capable of detecting and digitizing reflected light from a scene, and transmitting data to the CCU.

During camera operation, a PID control algorithm may be run to ensure that the captured scene maintains a desired video exposure level to maximize the dynamic range of the sensor or to achieve a desired scene response that the end-user desires. This control algorithm be generally known as Automatic Shutter Control (ASC). In some embodiments each light pulse, such as a laser pulse, may be adjusted proportionally to the error measurement of desired exposure level compared to a measured exposure level. This may be measured using the mean pixel value of all pixels or some portion of pixels from the Pixel Array (PA). The ASC may request adjustment to be made to the light pulse in duration and/or intensity to ensure that the desired setpoint is achieved in some specified time to not affect image quality.

In an embodiment the light source will be required to consistently deliver a specified light level to meet the request of the ASC algorithm. This range can be anywhere from $2$-$2^n$ bits, depending on the application precision requirements.

However, a problem may arise for the light source, due to warm-up requirements, changes in temperature at each light emitter or each laser, temperature in the box, manufacturing defects, or other typical issues associated with light emitters, such as lasers, and electronic devices that may prevent the light source from meeting the precision demands of the ASC algorithm leading to flickering light, image artifacting, or other undesirable effects causing poor image quality and/or a system unusable to the end-user. What is needed is a solution to ensure functional specification and performance demands are met to satisfy user experience.

In an embodiment a light sensing element, which may be a photo diode or another light sensing element, may be configured to read the energy transmission on individual fiber channels coming from each light emitter, such as a laser, to integrate the light energy in real-time, which is typically less than 1 ms. Each laser may have a single fiber ranging from 0.05 mm to 0.5 mm connected to an optical output from the laser. Laser can vary in wavelength and power and may be chosen to meet application need. The light sensing element, such as a photo diode, may be attached or directed to the passing fiber would provide an independent feedback that may then be compared to a register or variable retrieved from computer memory that comprises predetermined desired light levels requested by the AEC. This system may ensure that once a light energy level has been achieved the laser would be shut-off or disabled to preserve the desired image quality.

An embodiment may comprise a single photodiode sensing the electromagnetic energy of a multitude of fibers or a light sensing element, such as a photo diode or other light sensing element, looking at a single fiber individually. It is also understood that a user or system may need to calibrate this feedback to ensure precision requirements are met in the application. An example showing the control of two lasers is depicted in FIG. 1.

Figure 7:
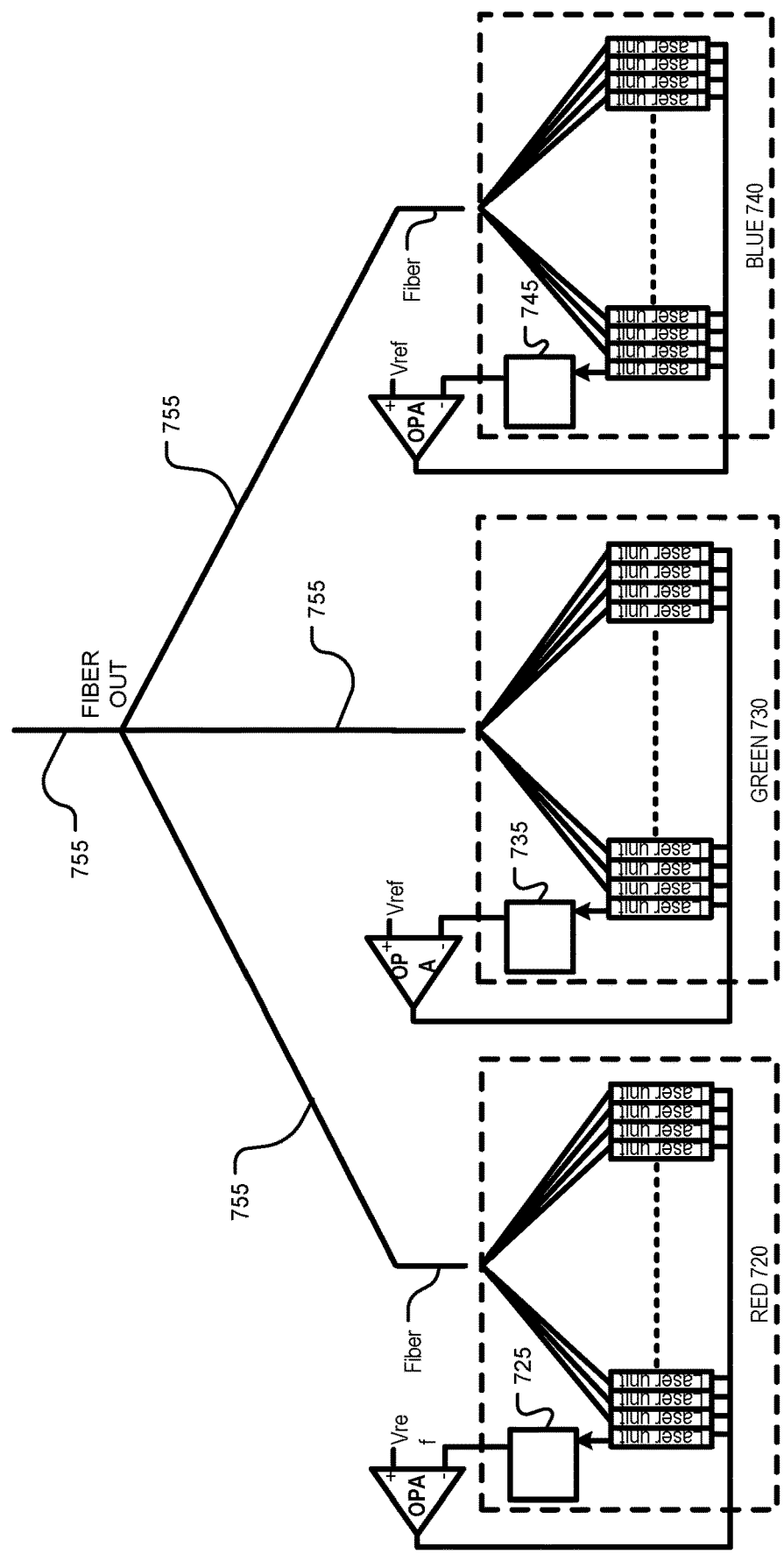
FIG. 7 illustrates an embodiment of a system having a plurality of laser emitters in accordance with the principles and teachings of the disclosure.

In an embodiment a light sensing element, such as a photo diode, may be placed internally on each laser module, such that there may be a system having a plurality of sensing elements, such as photo diodes. Since laser modules 155 are typically comprised of a plurality of lasers arranged in a linear array (as illustrated in FIG. 7) or other geometric pattern usually containing 10 or more individual laser diodes, to ensure precision light output of the laser module one could direct a small portion of those laser's outputs, say as little as one or two, to a sensing element 160 or any device that can transform light into a voltage or current level that would measure the amount of light output of one, two or N laser diode(s) that can be used with a differential amplifier comparing light output measurement from sensing element against a desired reference voltage or current level. This circuit may then provide direct feedback to the bias current (or voltage) of the laser module ensuring that desired output light level is met to a desired precision level. An example is shown in FIG. 2.

Figure 2:
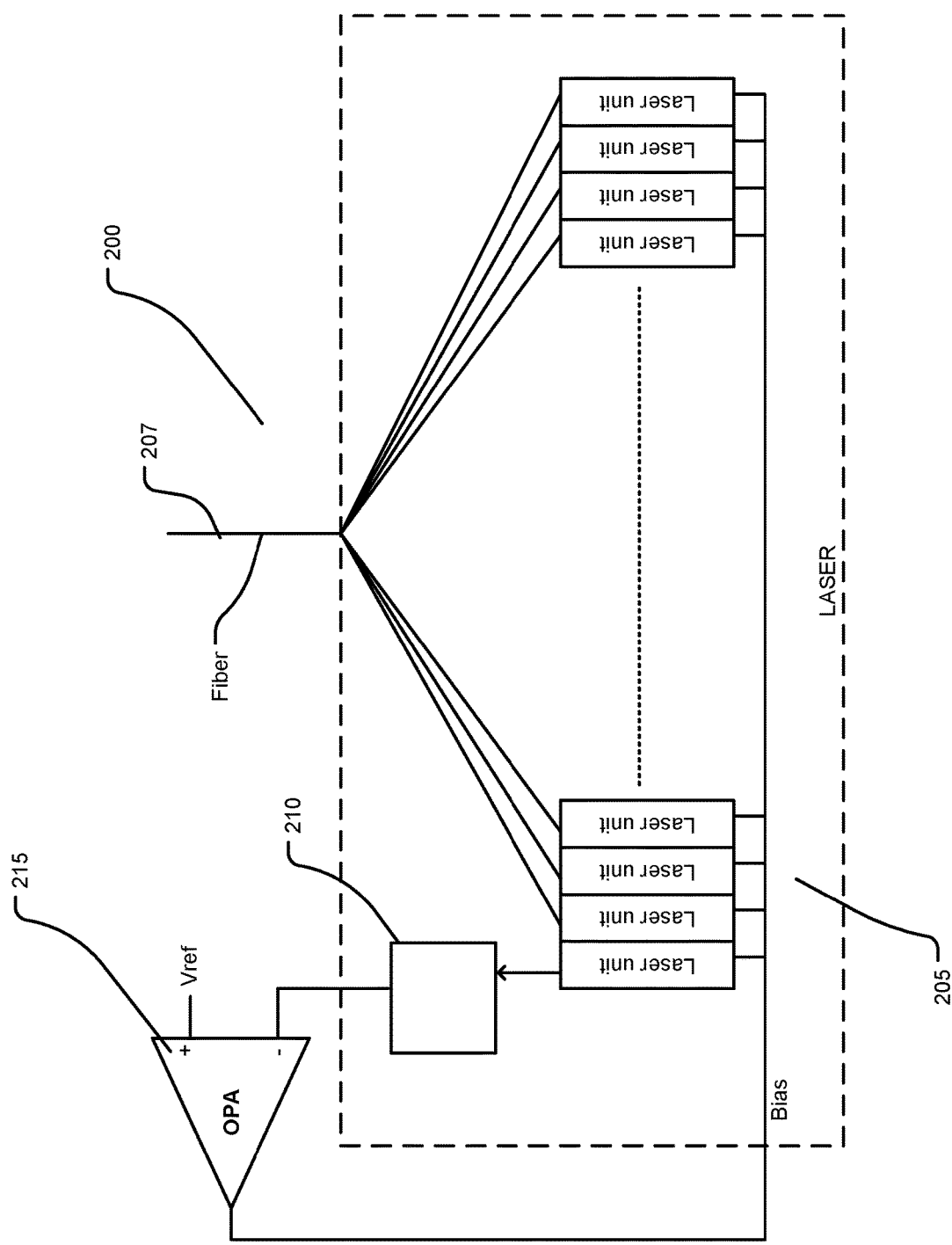
FIG. 2 illustrates an embodiment of a light controller of an illumination system in accordance with the principles and teachings of the disclosure.

As illustrated in FIG. 2, an embodiment may comprise a bundle of laser emitters 205 that are combined through the use of fiber optics 207. The system 200, may further comprise a light sensing element or an electromagnetic sensor 210 that senses the output of one of the lasers in the laser bundle 205. Additionally, feedback may also be applied with the use of a light frequency doubler or operation amplification circuit 215 has been incorporated into certain configurations of the laser module. For a non-limiting example, green or blue laser modules may be used in applications that could benefit from this device.

In an embodiment a precision level of the light output may be 0.01%-10% depending on the application requirements.

Figure 3:
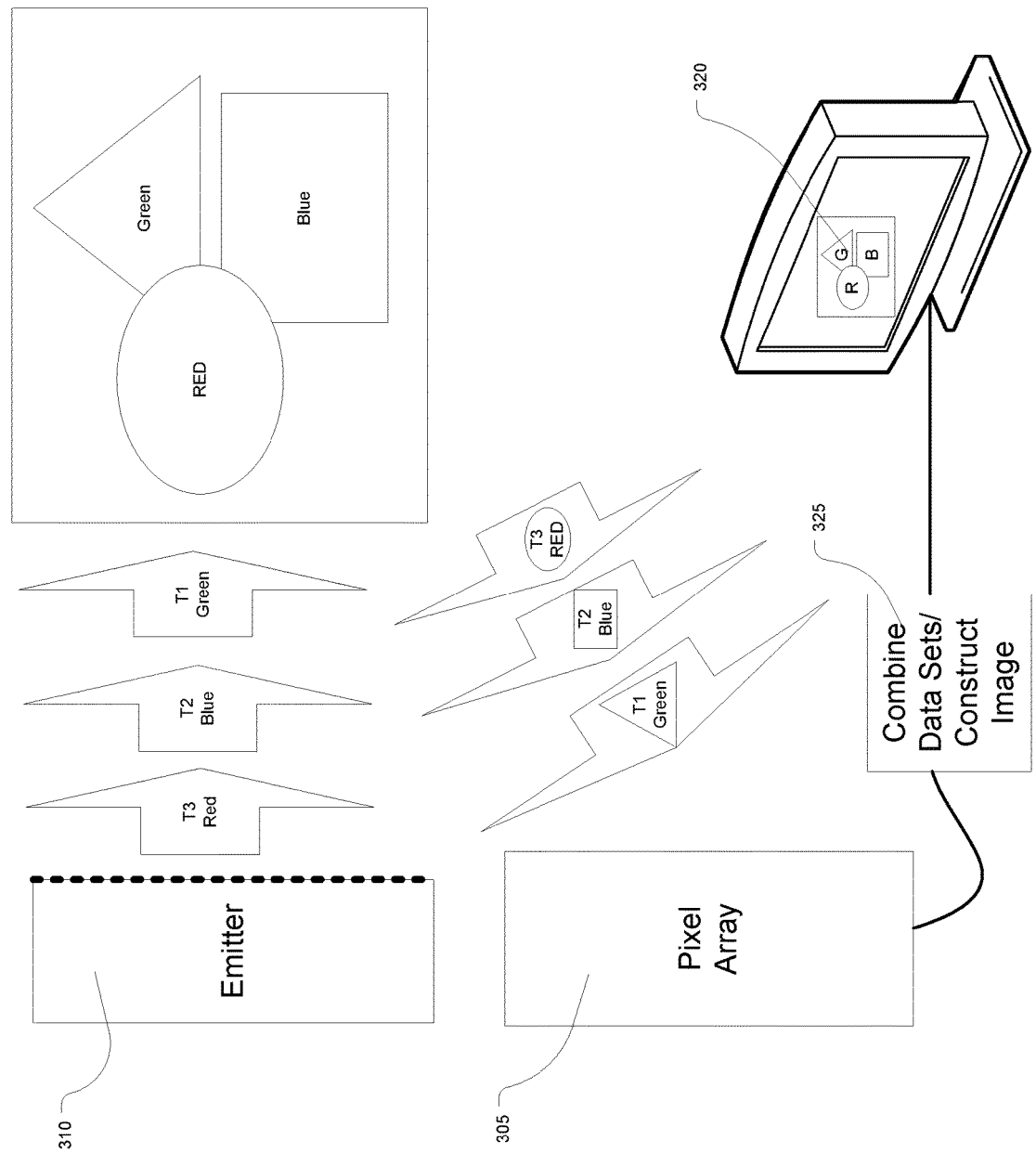
FIG. 3 is a schematic view of a system of a paired sensor and an electromagnetic emitter in operation for use in producing an image in a light deficient environment made in accordance with the principles and teachings of the disclosure.

FIG. 3 illustrates a schematic view of a paired sensor 305 and an electromagnetic emitter 310 in operation for use in producing an image in a light deficient environment. Such a configuration allows for increased functionality in light controlled or ambient light deficient environments. It should be noted that as used herein the term "light" is both a particle and a wavelength, and is intended to denote electromagnetic radiation that is detectable by a pixel array, and may be include wavelengths from the visible and non-visible spectrums of electromagnetic radiation. The term "partition" is used herein to mean a pre-determined range of wavelengths of the electromagnetic spectrum that is less than the entire spectrum, or in other words, wavelengths that make up some portion of the electromagnetic spectrum. An emitter may be a light source that is controllable as to the portion of the electromagnetic spectrum that is emitted, the intensity of the emissions, or the duration of the emission, or all three. An emitter may emit light in any dithered, diffused, or columnated emission and may be controlled digitally or through analog methods or systems.

A pixel array 305 of an image sensor may be paired with an emitter 310 electronically, such that they are synced during operation for both receiving the emissions and for the adjustments made within the system. As can be seen in FIG. 3, an emitter 310 may be tuned to emit electromagnetic radiation in the form of a laser, which may be pulsed in order to illuminate an object. The emitter 310 may pulse at an interval that corresponds to the operation and functionality of a pixel array 305. The emitter 310 may pulse light in a plurality of electromagnetic partitions, such that the pixel array receives electromagnetic energy and produces a data set that corresponds (in time) with each specific electromagnetic partition. For example, FIG. 3 illustrates a system having a monochromatic pixel array (black and white) 305, which is simply sensitive to electromagnetic radiation of any wavelength. The light emitter illustrated in the figure may be a laser emitter 310 that is capable of emitting a green electromagnetic partition, a blue electromagnetic partition, and a red electromagnetic partition in any desired sequence. It will be appreciated that other light emitters may be used in FIG. 3 without departing from the scope of the disclosure, such as digital or analog based emitters. During operation, the data created by the monochromatic sensor for any individual pulse is assigned a specific color partition, wherein the assignment is based on the timing of the pulsed color partition from the emitter. Even though the pixels are not color dedicated they can be assigned a color for any given data set based on timing. In one embodiment, three data sets representing RED, GREEN and BLUE pulses may then be combined to form a single image frame 320. It will be appreciated that the disclosure is not limited to any particular color combination or any particular electromagnetic partition, and that any color combination or any electromagnetic partition may be used in place of RED, GREEN and BLUE, such as Cyan, Magenta and Yellow, Ultraviolet, infra-red, or any other color combination, including all visible and non-visible wavelengths, without departing from the scope of the disclosure. In the figure, the object to be imaged contains a red portion, green portion and a blue portion. As illustrated in the figure, the reflected light from the electromagnetic pulses only contains the data for the portion of the object having the specific color that corresponds to the pulsed color partition. Those separate color (or color interval) data sets can then be used to reconstruct 325 the image by combining the data sets.

Figure 4:
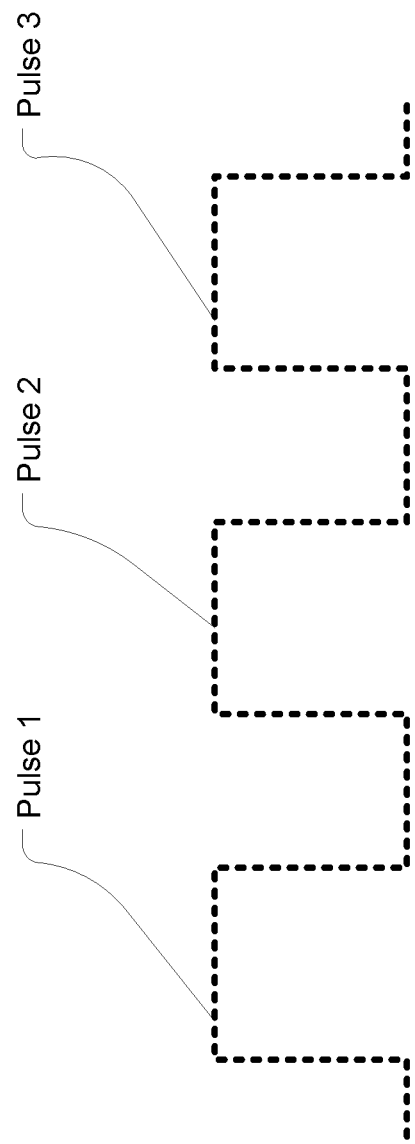
FIG. 4 is a graphical representation of the operation of an embodiment of an electromagnetic emitter in accordance with the principles and teachings of the disclosure.

FIG. 4 graphically illustrates the operation of an embodiment of an electromagnetic emitter. An emitter may be timed to correspond with the cycles of a sensor, such that electromagnetic radiation is emitted within the sensor operation cycle and/or during a portion of the sensor operation cycle. In an embodiment the emitter may pulse during the read out portion of the sensor operation cycle. In an embodiment the emitter may pulse during the blanking portion of the sensor operation cycle. In an embodiment the emitter may pulse for a duration that is during portions of two or more sensor operational cycles. In an embodiment the emitter may begin a pulse during the blanking portion, or during the optical black portion of the readout portion, and end the pulse during the readout portion, or during the optical black portion of the readout portion. It will be understood that any combination of the above is intended to fall within the scope of this disclosure as long as the pulse of the emitter and the cycle of the sensor correspond.

Figure 5:
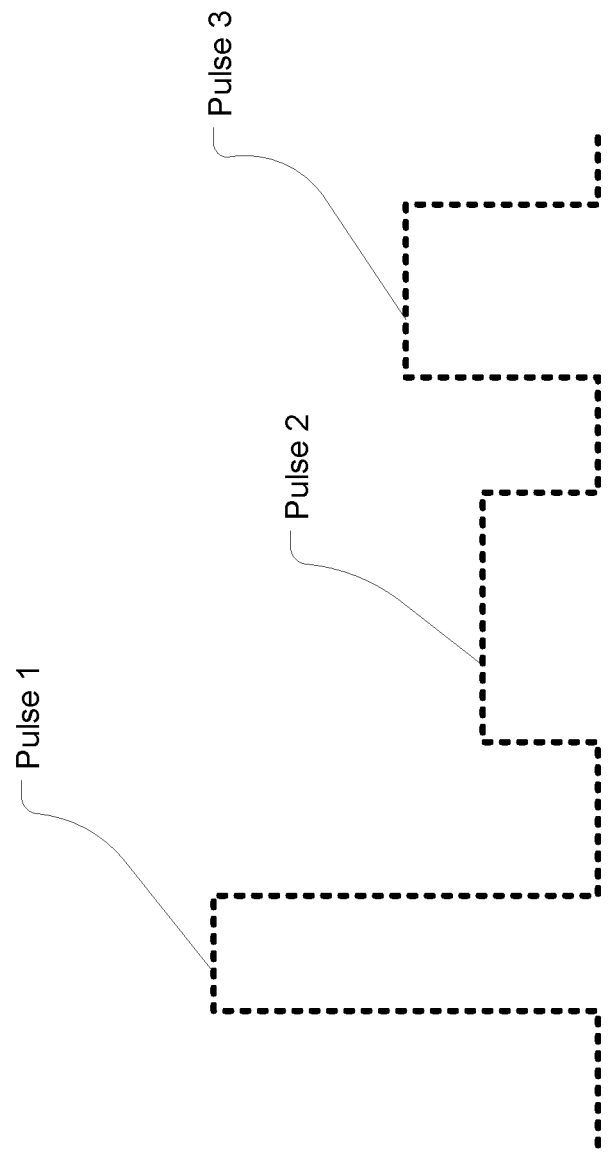
FIG. 5 is a graphical representation of varying the duration and magnitude of the emitted electromagnetic pulse in order to provide exposure control in accordance with the principles and teachings of the disclosure.

FIG. 5 graphically represents varying the duration and magnitude of the emitted electromagnetic pulse to control exposure. An emitter having a fixed output magnitude may be pulsed during any of the cycles noted above in relation to FIG. 3 for an interval to provide the needed electromagnetic energy to the pixel array. An emitter having a fixed output magnitude may be pulsed at a longer interval of time, thereby providing more electromagnetic energy to the pixels or the emitter may be pulsed at a shorter interval of time, thereby providing less electromagnetic energy. Whether a longer or shorter interval time is needed depends upon the operational conditions.

In contrast to adjusting the interval of time that the emitter pulses a fixed output magnitude, the magnitude of the emission itself may be increased in order to provide more electromagnetic energy to the pixels. Similarly, decreasing the magnitude of the pulse provides less electromagnetic energy to the pixels. It should be noted that an embodiment of the system may have the ability to adjust both magnitude and duration concurrently, if desired. Additionally, the sensor may be adjusted to increase its sensitivity and duration as desired for optimal image quality.

Implementations of the disclosure may comprise or utilize a special purpose or general-purpose computer including computer hardware, such as, for example, one or more processors and system memory, as discussed in greater detail below. Implementations within the scope of the disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions may be computer storage media (devices). Computer-readable media that carry computer-executable instructions may be transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" may be defined as one or more data links that enable the transport of electronic data between computer systems and/or modules and/or other electronic devices. In an implementation, a sensor and camera control unit may be networked in order to communicate with each other, and other components, connected over the network to which they may be connected. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures that can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered Storage, such as FusionIO). Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts may be disclosed as example forms of implementing the claims.

Those skilled in the art will appreciate that the disclosure may be practiced in network computing environments with many types of computer system configurations, including, personal computers, desktop computers, laptop computers, message processors, control units, camera control units, hand-held devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above mentioned computing devices may be provided by or located within a brick and mortar location. The disclosure may also be practiced in distributed system environments where local and remote computer systems, which may be linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays can be programmed to carry out one or more of the systems and procedures described herein. Certain terms may be used throughout the following description and Claims to refer to particular system components. As one skilled in the art will appreciate, components may be referred to by different names. This document does not intend to distinguish between components that differ in name, but not function.

Figure 6:
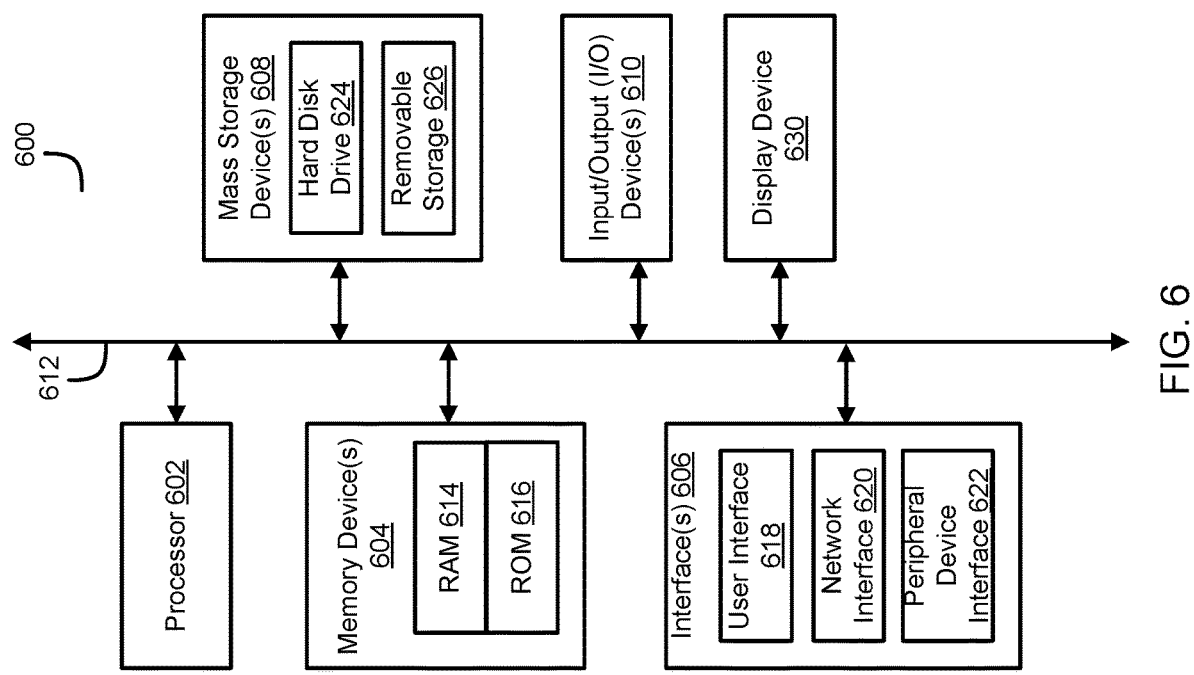
FIG. 6 illustrates an embodiment of hardware in accordance with the principles and teachings of the disclosure.

FIG. 6 is a block diagram illustrating an example computing device 600. Computing device 600 may be used to perform various procedures, such as those discussed herein. Computing device 600 can function as a server, a client, or any other computing entity. Computing device can perform various monitoring functions as discussed herein, and can execute one or more application programs, such as the application programs described herein. Computing device 600 can be any of a wide variety of computing devices, such as a desktop computer, a notebook computer, a server computer, a handheld computer, camera control unit, tablet computer and the like.

Computing device 600 includes one or more processor(s) 602, one or more memory device(s) 604, one or more interface(s) 606, one or more mass storage device(s) 608, one or more Input/Output (I/O) device(s) 610, and a display device 630 all of which may be coupled to a bus 612. Processor(s) 602 include one or more processors or controllers that execute instructions stored in memory device(s) 604 and/or mass storage device(s) 608. Processor(s) 602 may also include various types of computer-readable media, such as cache memory.

Memory device(s) 604 include various computer-readable media, such as volatile memory (e.g., random access memory (RAM) 614) and/or nonvolatile memory (e.g., read-only memory (ROM) 616). Memory device(s) 604 may also include rewritable ROM, such as Flash memory.

Mass storage device(s) 608 include various computer readable media, such as magnetic tapes, magnetic disks, optical disks, solid-state memory (e.g., Flash memory), and so forth. As shown in FIG. 6, a particular mass storage device is a hard disk drive 624. Various drives may also be included in mass storage device(s) 608 to enable reading from and/or writing to the various computer readable media. Mass storage device(s) 608 include removable media 626 and/or non-removable media.

I/O device(s) 610 include various devices that allow data and/or other information to be input to or retrieved from computing device 600. Example I/O device(s) 610 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 630 includes any type of device capable of displaying information to one or more users of computing device 600. Examples of display device 630 include a monitor, display terminal, video projection device, and the like.

Interface(s) 606 include various interfaces that allow computing device 600 to interact with other systems, devices, or computing environments. Example interface(s) 606 may include any number of different network interfaces 620, such as interfaces to local area networks (LANs), wide area networks (WANs), wireless networks, and the Internet. Other interface(s) include user interface 618 and peripheral device interface 622. The interface(s) 606 may also include one or more user interface elements 618. The interface(s) 606 may also include one or more peripheral interfaces such as interfaces for printers, pointing devices (mice, track pad, etc.), keyboards, and the like.

Bus 612 allows processor(s) 602, memory device(s) 604, interface(s) 606, mass storage device(s) 608, and I/O device(s) 610 to communicate with one another, as well as other devices or components coupled to bus 612. Bus 612 represents one or more of several types of bus structures, such as a system bus, PCI bus, IEEE 1394 bus, USB bus, and so forth.

For purposes of illustration, programs and other executable program components may be shown herein as discrete blocks, although it is understood that such programs and components may reside at various times in different storage components of computing device 600, and may be executed by processor(s) 602. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

FIG. 7 illustrates an implementation of a laser illumination system having a plurality of laser bundles emitting a plurality of wavelengths of electromagnetic energy. As can be seen in the figure, the illumination system 700 may comprise read laser bundle 720, a green laser bundle 730, and a blue laser bundle 740 that are all optically coupled together though fiber optics 755. As can be seen in the figure, each of the laser bundles may have a corresponding light sensing element or electromagnetic sensor 725, 735, 745 respectively, for sensing the output of the specific laser bundle or wavelength.

It will be appreciated that various features disclosed herein provide significant advantages and advancements in the art. The following embodiments may be exemplary of some of those features.

In the foregoing Detailed Description of the Disclosure, various features of the disclosure may be grouped together in a single embodiment for the purpose of streamlining the disclosure. This method of disclosure is not to be interpreted as reflecting an intention that the claimed disclosure requires more features than may be expressly recited in each claim. Rather, inventive aspects lie in less than all features of a single foregoing disclosed embodiment.

It is to be understood that the above-described arrangements may be only illustrative of the application of the principles of the disclosure. Numerous modifications and alternative arrangements may be devised by those skilled in the art without departing from the spirit and scope of the disclosure and the appended claims may be intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms may be used throughout the following description and Claims to refer to particular system components. As one skilled in the art will appreciate, components may be referred to by different names. This document does not intend to distinguish between components that differ in name, but not function.

The foregoing description has been presented for the purposes of illustration and description. It is not intended to be exhaustive or to limit the disclosure to the precise form disclosed. Many modifications and variations may be possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A system for providing illumination for an endoscopic device, the system comprising:
   a light source comprising a plurality of laser bundles, wherein each laser bundle comprises a plurality of laser light emitters, wherein the light source sequentially pulses electromagnetic energy in a plurality of individual electromagnetic partitions;
   an electromagnetic sensor embedded within the light source to sense electromagnetic energy emitted from at least one, but less than all, of the plurality of laser light emitters within each of the plurality of laser bundles; and
   a control circuit in electronic communication with the electromagnetic sensor and the at least one of the plurality of laser light emitters;
   wherein the electromagnetic sensor receives electromagnetic energy from at least one of the plurality of laser light emitters, and wherein the electromagnetic sensor measures an amount of electromagnetic energy generated by the at least one of the plurality of laser light emitters.

2. The illumination system of claim 1, wherein the electromagnetic sensor is a photo diode.

3. The illumination system of claim 1, wherein the control circuit is configured to cause the light source to pulse electromagnetic energy during a blanking portion of an image sensor's operation cycle and controls a duty cycle of the plurality of laser light emitters based on a predetermined, known output and in response to signals generated by the electromagnetic sensor that correspond to the amount of electromagnetic energy generated by the at least one of the plurality of laser light emitters to obtain a desired exposure response for images captured by the image sensor.

4. The illumination system of claim 1, wherein the plurality of laser bundles emits a plurality of wavelengths of electromagnetic energy.

5. The illumination system of claim 4, further comprising a plurality of electromagnetic sensors that each correspond to one of the plurality of wavelengths of electromagnetic energy.

6. The illumination system of claim 5, wherein the electromagnetic sensors can sense each of the plurality of laser light emitters independently.

7. The illumination system of claim 1, further comprising an operation amplifier circuit in electronic communication with the electromagnetic sensor.

8. The illumination system of claim 1, wherein the control circuit controls one or more of a duration and magnitude of the plurality of individual electromagnetic partitions pulsed by the light source to control exposure of the pulses of electromagnetic energy to thereby provide an amount of electromagnetic energy to an image sensor required by the system from one pulse to another pulse.

9. A system for use in a light deficient environment comprising:
   an endoscope;
   an image sensor to capture images of a scene; and
   a light illumination system comprising:
      a light source comprising a plurality of light bundles, wherein each light bundle comprises a plurality of light emitters, wherein the light source sequentially pulses electromagnetic energy in a plurality of individual electromagnetic partitions;
      an electromagnetic sensor embedded within the light source to sense electromagnetic energy emitted from at least one, but less than all, of the plurality of light emitters within each of the plurality of light bundles; and
      a control circuit in electronic communication with the electromagnetic sensor and the at least one of the plurality of light emitters;
      wherein the electromagnetic sensor receives electromagnetic energy from at least one of the plurality of light emitters, and wherein the electromagnetic sensor measures an amount of electromagnetic energy generated by the at least one of the plurality of light emitters;
   wherein the image sensor and the light illumination system are synchronized with regard to timing during operation.

10. The system of claim 9, wherein the electromagnetic sensor is a photo diode.

11. The system of claim 9, wherein the control circuit is configured to cause the light source to pulse electromagnetic energy during a blanking portion of the image sensor's operation cycle and controls a duty cycle of the light source in response to signals generated by the electromagnetic sensor that correspond to electromagnetic energy in the fiber optic cable that is generated by the light source to obtain a desired exposure response for images captured by the image sensor.

12. The system of claim 9, wherein the image sensor comprises a readout period, which includes an optical black portion, and a blanking period, and the control circuit is configured to cause the light source to start pulsing during the optical black portion of the readout period or end pulsing during the optical black portion of the readout period.

13. The system of claim 9, wherein the plurality of light bundles emits a plurality of wavelengths of electromagnetic energy.

14. The system of claim 13, further comprising a plurality of electromagnetic sensors each corresponding to one of the plurality of wavelengths of electromagnetic energy.

15. The system of claim 14, wherein the electromagnetic sensors sense each of the plurality of light emitters independently.

16. The system of claim 9, further comprising an operation amplifier circuit in electronic communication with the electromagnetic sensor.

17. The system of claim 9, wherein the control circuit controls one or more of a duration and magnitude of the plurality of individual electromagnetic partitions pulsed by the light source to control exposure of the pulses of electromagnetic energy to thereby provide an amount of electromagnetic energy to the image sensor required by the system from one pulse to another pulse.

18. An illumination system having a rapid duty cycle comprising:
- a light source comprising a plurality of light bundles, wherein each light bundle comprises a plurality of light emitters, wherein the light source sequentially pulses electromagnetic energy in a plurality of individual electromagnetic partitions;
- an electromagnetic sensor embedded within the light source to sense electromagnetic energy emitted from at least one, but less than all, of the plurality of light emitters within each of the plurality of light bundles; and
- a control circuit in electronic communication with the electromagnetic sensor and the at least one of the plurality of light emitters;
- wherein the electromagnetic sensor receives electromagnetic energy from at least one of the plurality of light emitters, such that the electromagnetic sensor measures an amount of electromagnetic energy generated by the at least one of the plurality of light emitters.

19. The illumination system of claim 18, wherein the electromagnetic sensor is a photo diode.

20. The illumination system of claim 18, wherein the control circuit is configured to cause the light source to pulse electromagnetic energy during a blanking portion of an image sensor's operation cycle and controls a duty cycle of the plurality of light emitters based on a predetermined, known output and in response to signals generated by the electromagnetic sensor that correspond to the amount of electromagnetic energy generated by the at least one of the plurality of light emitters to obtain a desired exposure response for images captured by the image sensor.

21. The illumination system of claim 18, wherein system further comprises an image sensor having a readout period, which includes an optical black portion, and a blanking period, and the control circuit is configured to cause one or more of the light emitters of the light source to start pulsing during the optical black portion of the readout period or end pulsing during the optical black portion of the readout period.

22. The illumination system of claim 18, wherein the plurality of light bundles emits a plurality of wavelengths of electromagnetic energy.

23. The illumination system of claim 22, further comprising a plurality of electromagnetic sensors each corresponding to one of the plurality of wavelengths of electromagnetic energy.

24. The illumination system of claim 23, wherein the electromagnetic sensors sense each of the plurality of light emitters independently.

25. The illumination system of claim 18, further comprising an operation amplifier circuit in electronic communication with the electromagnetic sensor.

26. The illumination system of claim 18, wherein the control circuit controls one or more of a duration and magnitude of the plurality of individual electromagnetic partitions pulsed by the light source to control exposure of the pulses of electromagnetic energy to thereby provide an amount of electromagnetic energy to an image sensor required by the system from one pulse to another pulse.

* * * * *